(12) United States Patent
Carlsson et al.

(10) Patent No.: US 11,839,566 B2
(45) Date of Patent: *Dec. 12, 2023

(54) RESISTANCE SENSOR FOR IDENTIFYING LEAK LOCATIONS IN OSTOMY SYSTEM

(71) Applicant: Hollister Incorporated, Libertyville, IL (US)

(72) Inventors: Jonas P. Carlsson, Chicago, IL (US); Scott E. Liddle, Raleigh, NC (US); Kyle A. Matthews, Chapel Hill, NC (US)

(73) Assignee: Hollister Incorporated, Libertyville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/878,684

(22) Filed: Aug. 1, 2022

(65) Prior Publication Data

US 2022/0362050 A1 Nov. 17, 2022

Related U.S. Application Data

(63) Continuation of application No. 17/617,672, filed as application No. PCT/US2021/041283 on Jul. 12, 2021, now Pat. No. 11,432,956.

(Continued)

(51) Int. Cl.
*A61F 5/445* (2006.01)
*G01M 3/16* (2006.01)
(Continued)

(52) U.S. Cl.
CPC ............. *A61F 5/445* (2013.01); *A61F 5/443* (2013.01); *A61F 5/4404* (2013.01); *G01M 3/16* (2013.01)

(58) Field of Classification Search
CPC ........ A61F 5/445; A61F 5/443; A61F 5/4404; G01M 3/16
See application file for complete search history.

(56) References Cited

U.S. PATENT DOCUMENTS 5,015,958 A     5/1991 Masia
5,111,812 A  *  5/1992 Swanson ............... A61N 1/0563
                                                    607/2

(Continued)

FOREIGN PATENT DOCUMENTS

EP     3727219 A1    10/2020
GB     2343628 A      5/2000
(Continued)

OTHER PUBLICATIONS

"Notification of Transmittal of the International Search Report and the Written Opinion of the International Searching Authority, or the Declaration", ISA/EPO, Nov. 4, 2021.

(Continued)

*Primary Examiner* — Guy K Townsend
(74) *Attorney, Agent, or Firm* — Levenfeld Pearlstein, LLC

(57) ABSTRACT

A sensor device for identifying an ostomy effluent leak location in an ostomy system includes a stoma opening and electrically conductive circuitry arranged in pattern around the stoma opening. The electrically conductive circuitry includes a first electrode and a second electrode spaced from the first electrode. The first electrode is subdivided by a plurality of resistors spaced along a length of the first electrode. The second electrode extends as a continuous strip of conductive material. The sensor device is configured to detect electrical resistance in the electrically conductive circuit and identify a location of a leak based on the detected electrical resistance.

20 Claims, 5 Drawing Sheets

Related U.S. Application Data

(60) Provisional application No. 63/052,132, filed on Jul. 15, 2020.

(51) Int. Cl.
  *A61F 5/443* (2006.01)
  *A61F 5/44* (2006.01)

(56) References Cited

U.S. PATENT DOCUMENTS

| | | | |
|---|---|---|---|
| 5,237,995 A * | 8/1993 | Cano | A61B 5/28 600/397 |
| 6,038,914 A | 3/2000 | Carr | |
| 6,171,289 B1 * | 1/2001 | Millot | A61F 5/443 604/336 |
| 6,461,329 B1 | 10/2002 | Van Antwerp | |
| 6,485,476 B1 * | 11/2002 | von Dyck | A61F 5/441 604/332 |
| 8,235,930 B1 | 8/2012 | McCall | |
| 8,398,603 B2 * | 3/2013 | Thirstrup | A61B 5/746 602/41 |
| 9,119,916 B2 | 9/2015 | Heppe | |
| 9,216,104 B2 * | 12/2015 | Thirstrup | A61F 5/4404 |
| 10,016,298 B2 * | 7/2018 | Thirstrup | A61F 13/42 |
| 10,987,243 B2 * | 4/2021 | Thirstrup | A61B 5/746 |
| 11,096,818 B2 * | 8/2021 | Thirstrup | A61F 13/02 |
| 11,141,100 B2 * | 10/2021 | Schoess | A61B 5/6813 |
| 11,298,063 B2 * | 4/2022 | Tran | A61F 5/4404 |
| 11,432,956 B1 * | 9/2022 | Carlsson | G01M 3/16 |
| 2003/0132763 A1 * | 7/2003 | Ellenz | G01V 3/088 324/663 |
| 2007/0185464 A1 * | 8/2007 | Fattman | A61L 24/043 604/336 |
| 2008/0275327 A1 * | 11/2008 | Faarbaek | A61B 5/6833 600/382 |
| 2008/0300559 A1 * | 12/2008 | Gustafson | A61F 13/42 604/361 |
| 2010/0030167 A1 * | 2/2010 | Thirstrup | A61F 5/4404 340/657 |
| 2010/0072271 A1 * | 3/2010 | Thorstensson | A61F 13/42 235/375 |
| 2013/0030397 A1 * | 1/2013 | Sabeti | A61F 5/4405 604/338 |
| 2013/0150769 A1 * | 6/2013 | Heppe | A61M 1/3656 604/6.16 |
| 2013/0231620 A1 * | 9/2013 | Thirstrup | A61F 5/445 604/344 |
| 2014/0288381 A1 * | 9/2014 | Faarbaek | A61B 5/0002 600/300 |
| 2015/0250639 A1 * | 9/2015 | Thirstrup | A61F 13/00051 156/278 |
| 2015/0257923 A1 * | 9/2015 | Thirstrup | A61F 13/42 604/318 |
| 2017/0340474 A1 * | 11/2017 | Thirstrup | A61B 5/746 |
| 2019/0133811 A1 * | 5/2019 | Seres | A61B 5/746 |
| 2019/0192066 A1 * | 6/2019 | Schoess | A61B 5/443 |
| 2019/0192332 A1 | 6/2019 | Hansen et al. | |
| 2019/0192333 A1 | 6/2019 | Hansen et al. | |
| 2019/0192334 A1 | 6/2019 | Hansen et al. | |
| 2020/0113556 A1 * | 4/2020 | Paulus | A61B 17/32056 |
| 2020/0246176 A1 | 8/2020 | Hansen et al. | |
| 2020/0306074 A1 | 10/2020 | Speiermann et al. | |
| 2020/0330260 A1 | 10/2020 | Hansen et al. | |
| 2020/0375786 A1 | 12/2020 | Hansen et al. | |
| 2020/0383637 A1 * | 12/2020 | Hansen | A61B 5/6832 |
| 2021/0007881 A1 | 1/2021 | Svanegaard et al. | |
| 2021/0113130 A1 * | 4/2021 | Tran | A61B 5/1032 |
| 2021/0267814 A1 * | 9/2021 | Schoess | A61F 13/42 |
| 2021/0338471 A1 * | 11/2021 | Nolan | A61F 5/4404 |
| 2021/0361465 A1 | 11/2021 | Hansen et al. | |
| 2021/0369490 A1 | 12/2021 | Hansen et al. | |

FOREIGN PATENT DOCUMENTS

| | | | | |
|---|---|---|---|---|
| WO | 2019120433 A1 | 6/2019 | | |
| WO | WO-2019120433 A1 * | 6/2019 | | A61B 5/0002 |
| WO | 2022063379 A1 | 3/2022 | | |

OTHER PUBLICATIONS

International Preliminary Report on Patentability issued by WIPO in connection with PCT/US2021/041283 dated Jan. 26, 2023.

* cited by examiner

RESISTANCE SENSOR FOR IDENTIFYING LEAK LOCATIONS IN OSTOMY SYSTEM

BACKGROUND

The following description relates generally to a sensor device for identifying leak locations for medical devices such as ostomy systems.

An ostomy pouch system typically includes a pouch formed from opposing sidewalls defining an internal collection area, an inlet opening for receiving a stoma, and an ostomy appliance for attaching the pouch to a user. The ostomy appliance may include, for example, an ostomy barrier of a one-piece pouch system, which is attached to one of the pouch sidewalls proximate an inlet opening, a faceplate for a two-piece pouch system configured to releasably engage a pouch, and a barrier ring. The ostomy appliance may include a skin barrier material for adhering to and sealing against user's peristomal skin surrounding the stoma.

The ostomy appliance may be susceptible to ostomy effluent leakage, and the seal formed between the skin barrier material and the user may weaken. Often times, the user may be unaware of or cannot easily assess an extent of weakening in the seal. Thus, the user may not become aware of a weakened seal, and consequently, the ostomy effluent may leak through to an exterior of the ostomy appliance.

Accordingly, it is desirable to provide a sensor device for an ostomy system configured to identify a leak and/or a leak location.

SUMMARY

In one aspect, a sensor device for identifying an ostomy effluent leak location in an ostomy system may include a stoma opening and electrically conductive circuitry arranged in pattern around the stoma opening. The electrically conductive circuitry may include a first electrode and a second electrode spaced from the first electrode. The first electrode may be subdivided by a plurality of resistors spaced along a length of the first electrode. The second electrode may extend as a continuous strip of conductive material. The sensor device may be configured to detect electrical resistance in the electrically conductive circuit and identify a location of a leak based on the detected electrical resistance.

In an embodiment, the electrically conductive circuitry may be arranged in a spiral pattern around the stoma opening. The electrically conductive circuitry may be a sensor layer and the sensor device may further include a substrate layer on which the sensor layer is applied. The sensor device may further include an adhesive layer. The sensor layer may be disposed between the adhesive layer and the substrate layer.

In an embodiment, the resistors of the plurality of resistors each may have a resistance significantly higher than a generalized resistance of the leak.

In another aspect, a sensor device for detecting an effluent leakage in a medical appliance may include an electrically conductive circuitry comprising a first electrode and a second electrode, which is arranged spaced apart from the first electrode, and an adhesive layer configured to attach the sensor device to user's skin. The first electrode may be subdivided by a plurality of resistors spaced along a length of the first electrode. The second electrode may extend as a continuous strip of conductive material. The sensor device may be configured to measure electrical resistance in the electrically conductive circuitry and determine a location of an effluent leakage based on a resistance measurement.

In an embodiment, the plurality of resistors may include R1, R2, and R3, wherein an effluent leakage may have a generalized leak resistance RL. The sensor device may be configured such that a total resistance ($R_{total}$) of the electrically conductive circuitry may drop significantly when an effluent leakage bridges the first and second electrodes. In such an embodiment, $R_{total}$ when no effluent leakage bridges the first and second electrodes may be at least 10 times greater than $R_{total}$ when an effluent leakage bridges the first electrode and the second electrode. In an embodiment, $R_{total}$ when an effluent leakage bridges the first and second electrodes between R1 and R2 may be R1+RL. $R_{total}$ when an effluent leakage bridges the first and second electrodes between R2 and R3 may be R1+R2+RL. $R_{total}$ when an effluent leakage bridges the first and second electrodes beyond R3 may be R1+R2+R3+RL.

In some embodiments, the sensor device may be configured to detect an ostomy effluent leakage and may include an opening for receiving a stoma. In such embodiments, the first electrode and the second electrode may be arranged in a spiral pattern around the opening. The sensor device may be configured to determine a progress of an ostomy effluent leakage, wherein the ostomy effluent leakage may propagate from proximate the opening to an outer periphery of the sensor device.

In an embodiment, the first electrode may be arranged in a spiral pattern having a plurality wraps around the opening. The second electrode may extend between the wraps of the first electrode. In such an embodiment, the first electrode may be arranged to have more wraps than the second electrode, wherein the radially innermost wrap and the radially outermost wrap are both formed by the first electrode. The plurality of resistors may comprise R1, R2 . . . $R_{n-2}$, $R_{n-1}$, and $R_n$, wherein the $R_n$ may be arranged on the radially innermost wrap of the first electrode. $R_{n-1}$ may be arranged adjacent and spaced apart from $R_n$. $R_{n-2}$ may be arranged adjacent and spaced apart from $R_{n-1}$. R1 may be arranged on the outermost wrap of the first electrode.

In an embodiment, the sensor device may be configured to detect a moderate leak when an ostomy effluent leakage bridges an innermost wrap of the first electrode and the second electrode. For example, $R_{total}$ when an effluent leakage bridges the first and second electrodes between $R_{n-1}$ and $R_{n-2}$ may be R1+R2 . . . +$R_{n-2}$+RL, which may indicate a moderate leak. The sensor device may also be configured to detect a critical leak when an ostomy effluent leakage bridges an outermost wrap of the first electrode and the second electrode. For example, $R_{total}$ when an effluent leakage bridges the first and second electrodes between $R_2$ and $R_3$ may be approximately R1+R2, which may indicate a critical leak.

The sensor device may further include a substrate layer, wherein the electrically conductive circuitry may be arranged between the substrate layer and the adhesive layer. The adhesive layer may be formed from a hydrocolloid adhesive.

In any of the foregoing embodiments, the sensor device may be provided as an ostomy accessory, wherein a distal side of the sensor device may be secured to a body side of an ostomy barrier.

Other objects, features, and advantages of the disclosure will be apparent from the following description, taken in conjunction with the accompanying sheets of drawings, wherein like numerals refer to like parts, elements, components, steps, and processes.

DETAILED DESCRIPTION

Figure 1A:
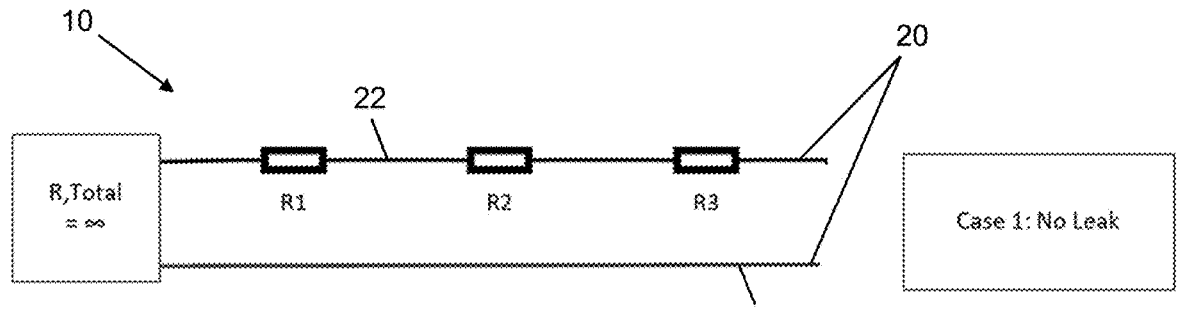
FIGS. 1A-1D are schematic diagrams illustrating examples of electrically conductive circuitry of a sensor device and ostomy effluent leaks at different locations along the circuitry according to embodiments.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

According to embodiments described herein, a sensor device is provided for an ostomy appliance. The sensor device may be configured to detect an ostomy effluent leak and/or identify a location of the ostomy effluent leak. The sensor device may be part of a leakage detection system for an ostomy appliance.

The sensor device may include electrically conductive circuitry. In an embodiment, the electrically conductive circuitry may include a first electrode and a second electrode spaced from the first electrode. The first electrode may be subdivided by one or more resistors. The second electrode may extend continuously as a strip of highly conductive material. That is, the second electrode may be free of resistors. The electrically conductive circuitry may be arranged in a predetermined pattern relative to a stoma opening extending through the sensor device. In use, the electrical resistance in the electrically conductive circuitry, for example between the first electrode and the second electrode, is relatively high when there is no leakage of ostomy effluent. However, the electrical resistance may decrease significantly when leaking ostomy effluent bridges the first and second electrodes.

The sensor device may detect the electrical resistance in the electrically conductive circuit. In embodiments, detecting the electrical resistance may include determining an electrical resistance value, for example, by calculating, approximating or measuring the electrical resistance value. In embodiments, the sensor device may also determine a change in electrical resistance as a function of time based on a series of detected electrical resistances. The sensor device may determine whether an ostomy effluent leak is present based on the detected electrical resistance. Alternatively, or in addition, the sensor device may identify a location of an ostomy effluent leak based on the detected electrical resistance. In an embodiment, the sensor device may determine the total resistance in the electrically conductive circuitry based on the resistance of individual resistors and a generalized leak resistance (i.e., electrical resistance of an ostomy effluent leak).

In an embodiment, the sensor device may include or be operably connected to a power supply configured to apply a current to the electrically conductive circuitry. In addition, the sensor device may include or be operably connected to a controller.

The controller may include, for example, a processor and a memory. The processor may be, for example, a microprocessor or other suitable computer processor or processor-like device. The processor may be configured to execute program instructions and perform operations based on the executed program instructions. For example, the processor may be configured to perform various operations described in the embodiments herein, such as, but not limited to, detect the electrical resistance in the electrically conductive circuitry, determine a change in the electrical resistance between the first and second electrodes as a function of time based on the detected electrical resistance, determine whether an ostomy effluent leak is present based on the detected electrical resistance, and/or identify a location of an ostomy effluent leak based on the detected electrical resistance.

The memory may be a non-transitory computer-readable storage medium configured to store the program instructions. The memory may also store other information, such as, but not limited to, resistor information. The resistor information may include, for example, a resistance and a position of each resistor. The memory may also store the detected electrical resistance including a series of detected electrical resistances detected as a function of time. In an embodiment, the controller and sensor device may be provided as an integrated component. Alternatively, the sensor device and the controller may be separate components operably connected to one another to form at least a portion of a leakage detection system. For ease of reference, in embodiments, descriptions of components and/or operations performed by the sensor device may include components and/or operations performed by sensor device, the controller or both.

FIGS. 1A-1D are schematic diagrams illustrating examples of electrically conductive circuitry 20 of a sensor device 10 and ostomy effluent leaks L1, L2 . . . Li at different locations P1, P2 . . . Pi along the electrically conductive circuitry 20 according to embodiments. Referring generally for FIGS. 1A-1D, the electrically conductive circuitry 20 may include a first electrode 22 and a second electrode 24 spaced from the first electrode 22. The electrically conductive circuitry 20 may also include at least one resistor R1, R2 . . . Ri disposed along the first electrode 22 to subdivide the first electrode 22. The second electrode 24 may be a continuous strip of highly conductive material. The first electrode 22 and the second electrode 24 may be arranged in a predetermined pattern or shape. In an embodiment, the first electrode 22 and the second electrode may be arranged in respective spiral patterns (FIG. 2).

In embodiments, electrical resistance in the electrically conductive circuitry 20, for example, between the first electrode 22 and the second electrode 24, may decrease significantly when an ostomy effluent leak bridges the first and second electrodes 22, 24. An exact value of the electrical resistance depends on the circuit design and characteristics of the leaking effluent. For example, in an embodiment, the electrical resistance may drop to about 100Ω or less in response to an ostomy effluent leak. However, the present description is not limited to such an example.

The electrical resistance values of the resistors R1, R2 . . . Ri may be selected to be significantly larger than the electrical resistance of an ostomy effluent leak, but small enough to minimize circuit impedance. For example, the resistors R1, R2 . . . Ri may have electrical resistance values of about 10 kΩ. The resistors R1, R2 . . . Ri may be added to the electrically conductive circuitry as additional components or may be created using one or more printed inks. An ostomy effluent leak may have a generalized leak resistance RL.

Figure 2:
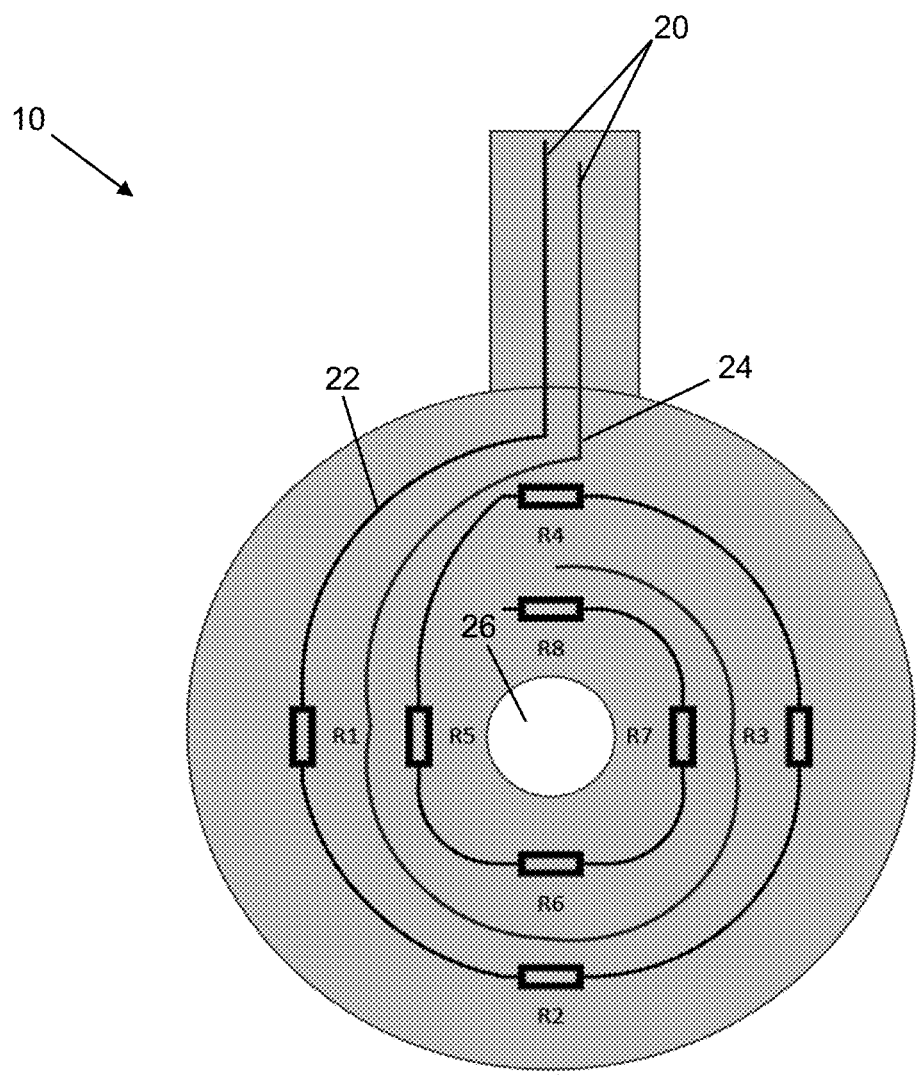
FIG. 2 is a diagram illustrating a plan view of a sensor device according to an embodiment.

FIG. 1A schematically illustrates an example in which there is no ostomy effluent leak bridging the first electrode 22 and the second electrode 24. Accordingly, the total electrical resistance $R_{TOTAL}$ is relatively high or approaches infinity. Based on the relatively high electrical resistance, the sensor device 10 may determine that an ostomy effluent leak is not present and thus, a location of an ostomy effluent leak is not present either.

Figure 1B:
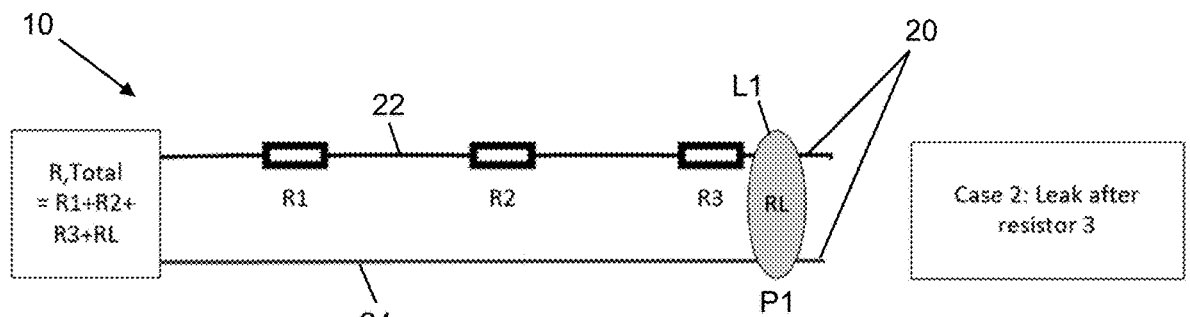

FIG. 1B schematically illustrates an example in which an ostomy effluent leak L1 between the first electrode 22 and the second electrode 24 is present at a location P1 beyond, for example, a third resistor R3. In the example of FIG. 1B, the total resistance $R_{TOTAL}$ may be calculated as:

$$R_{TOTAL}=R1+R2+R3+RL$$

In the example of FIG. 1B, the sensor device 10 may detect the ostomy effluent leak L1 and/or determine the location of the ostomy effluent leak L1 to be at a position after the third resistor R3 based on the total resistance $R_{TOTAL}$.

Figure 1C:
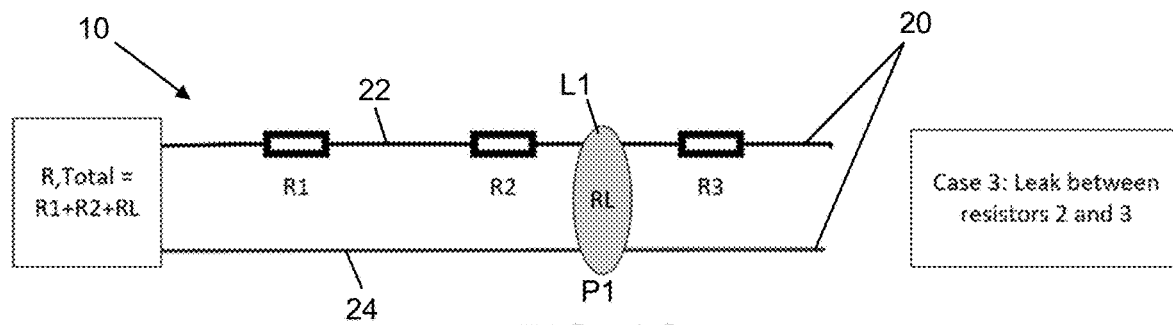

FIG. 1C schematically illustrates an example in which an ostomy effluent leak L1 bridging the first electrode 22 and the second electrode 24 is present at a location P1, for example, between a second resistor R2 and a third resistor R3. In the example of FIG. 1C, the total resistance $R_{TOTAL}$ may be calculated as:

$$R_{TOTAL}=R1+R2+RL$$

In the example of FIG. 1C, the sensor device 10 may detect the ostomy effluent leak L1 and/or determine the location of the ostomy effluent leak L1 to be at a position between the second and third resistors R2, R3 based on the total resistance $R_{TOTAL}$. In an embodiment, the generalized electrical resistance RL is less than the electrical resistance of any of the resistors R1, R2 . . . Ri connected in series. Thus, the sensor device 10 may distinguish the location of the ostomy effluent leak L1 in the example of FIG. 1C from the location of the ostomy effluent leak L1 in the example of FIG. 1B, for instance, based on the total resistance $R_{TOTAL}$ determined for each example.

Figure 1D:
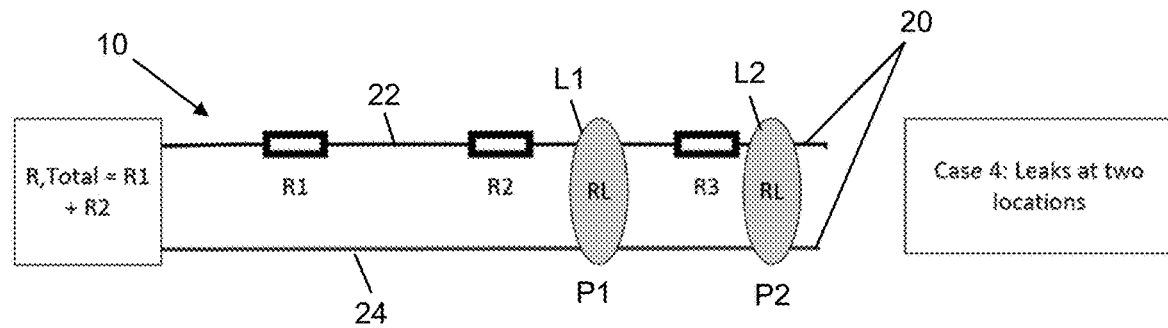

FIG. 1D schematically illustrates an example which ostomy effluent leaks L1, L2 bridging the first electrode 22 and the second electrode 24 are present at multiple locations P1, P2. For instance, in the example of FIG. 1D, a first ostomy effluent leak L1 may be located at a first position P1 between a second resistor R2 and a third resistor R3. A second ostomy effluent leak L2 may be located at a second position P2 beyond the third resistor R3. In some instances, multiple ostomy effluent leaks may be difficult to distinguish from a single leak at a location closest to the point electrical resistance is measured. The total resistance $R_{TOTAL}$ may be calculated as:

$$R_{TOTAL}=(R1+R2+1)/((1/RL)+1/(R3+RL))$$

However, if RL is small relative to the resistance values of the resistors R1, R2, R3 . . . Ri, the total resistance may be approximated as:

$$R_{TOTAL} \approx R1+R2$$

It will be appreciated that the diagrams of FIGS. 1A-1D are provided for the purposes of illustrative examples, and the present description is not limited to these examples. For example, the electrically conductive circuitry 20 may include any suitable number of resistors, R1, R2 . . . Ri, spaced at desired length intervals, some, all or none of which may be equal. In addition, any number of ostomy effluent leaks L1, L2 . . . Li may be detected. Further, the first electrode 22 and the second electrode 24 may extend in any suitable predetermined shape or pattern and may be spaced apart by any suitable distance. In an embodiment, the distance between the first electrode 22 and the second electrode 24 may be substantially the same along the respective lengths of the first and second electrodes 22, 24 or may vary in a desired manner.

FIG. 2 is a diagram illustrating a plan view of a sensor device according to an embodiment. Difficulty distinguishing multiple leaks may be mitigated in the present embodiments. For example, the electrically conductive circuitry 20 may be arranged within an ostomy barrier so that ostomy effluent leaks with the highest risk are nearest to the point of electrical resistance measurement.

Referring to the example shown in FIG. 2, the first and second electrodes 22, 24 may be arranged in a spiral around a stoma opening 26 configured to receive a stoma. That is, the electrically conductive circuitry 20 may be designed so leaks typically progress from a distal end of the electrodes 22, 24 nearest the stoma opening 26 to a proximal end, further from the stoma opening 26.

In an embodiment, the first electrode 22 may be arranged in a spiral pattern having a plurality wraps around the stoma opening 26. For example, as shown in FIG. 2, the first electrode 22 may generally be arranged in a spiral having two wraps. However, it is understood that the spiral of the first electrode 22 may include fewer or additional wraps. The second electrode 24 may also be arranged as a spiral. In an embodiment, the second electrode extends between wraps of the first electrode. In an embodiment, the first electrode 22 may be arranged to have more wraps than the second electrode 24. For example, the electrically conductive circuitry 20 may be arranged in a spiral configuration in which in the radially innermost and radially outermost wraps, relative to the stoma opening 26, are formed by the first electrode 22.

Figure 3:
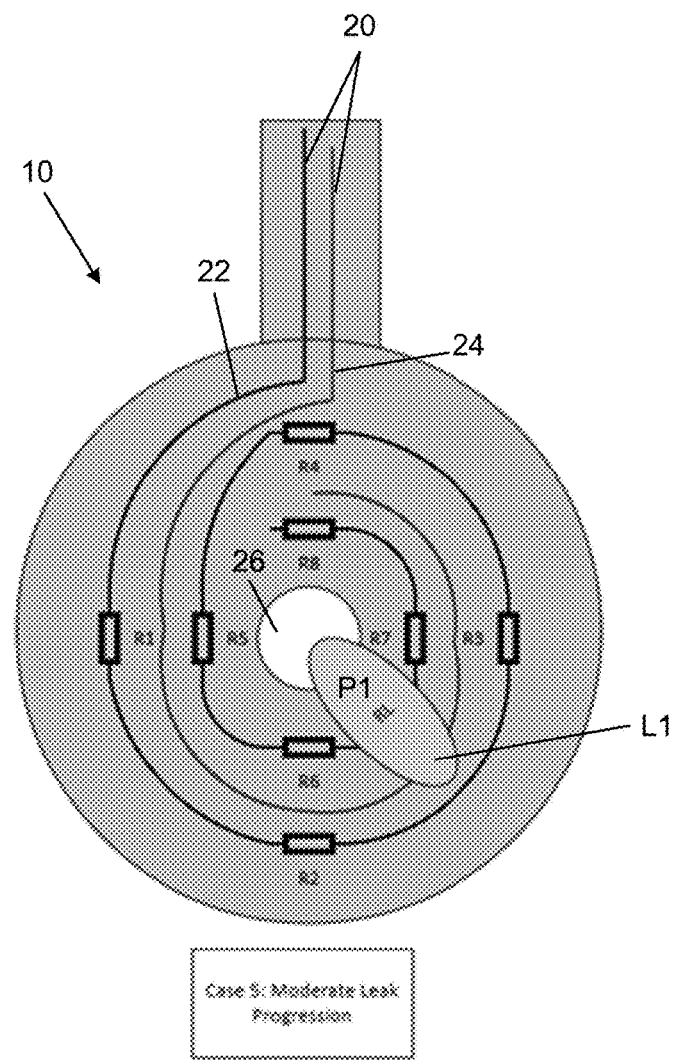
FIG. 3 is a diagram illustrating a plan view of a sensor device and an example of an ostomy effluent leak according to an embodiment.

FIG. 3 is a diagram illustrating a plan view of a sensor device 10 and an example of an ostomy effluent leak L1 according to an embodiment. The ostomy effluent leak L1 may be located at a position P1 and may have a generalized electrical resistance RL. The ostomy effluent leak L1 as shown in FIG. 3 may be considered to be a moderate leak.

Figure 4:
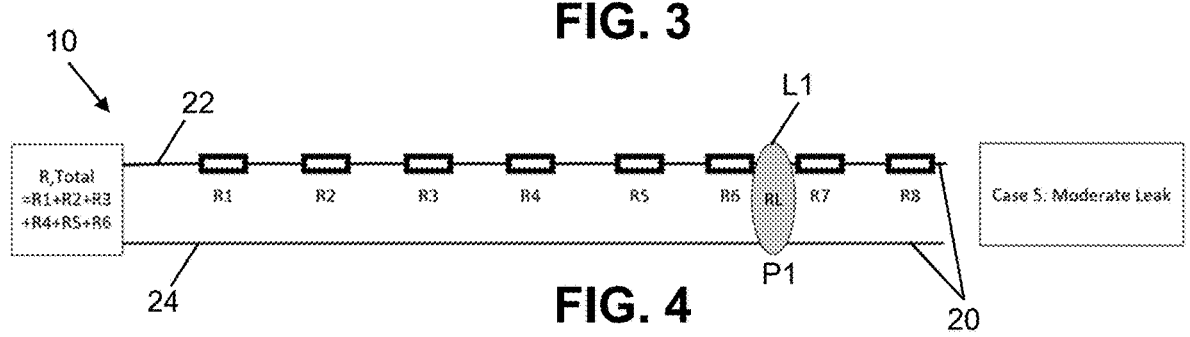
FIG. 4 is a schematic diagram illustrating the sensor device of FIG. 3 with the ostomy effluent leak disposed relative to electrically conductive circuitry of the sensor device.

FIG. 4 is a schematic diagram illustrating the sensor device 10 of FIG. 3 with the ostomy effluent leak L1 disposed relative to electrically conductive circuitry 20 of the sensor device 10. As shown in the examples of FIGS. 3 and 4, the ostomy effluent leak L1 may extend from the stoma opening 26 across the first electrode 22 between a sixth resistor R6 and a seventh resistor R7, and bridge the first and second electrodes 22, 24 between a first wrap of the first electrode 22 and the wrap of the second electrode 24. In such an example, the total resistance $R_{TOTAL}$ may be calculated as:

$$R_{TOTAL}=R1+R2+R3+R4+R5+R6+RL$$

Figure 5:
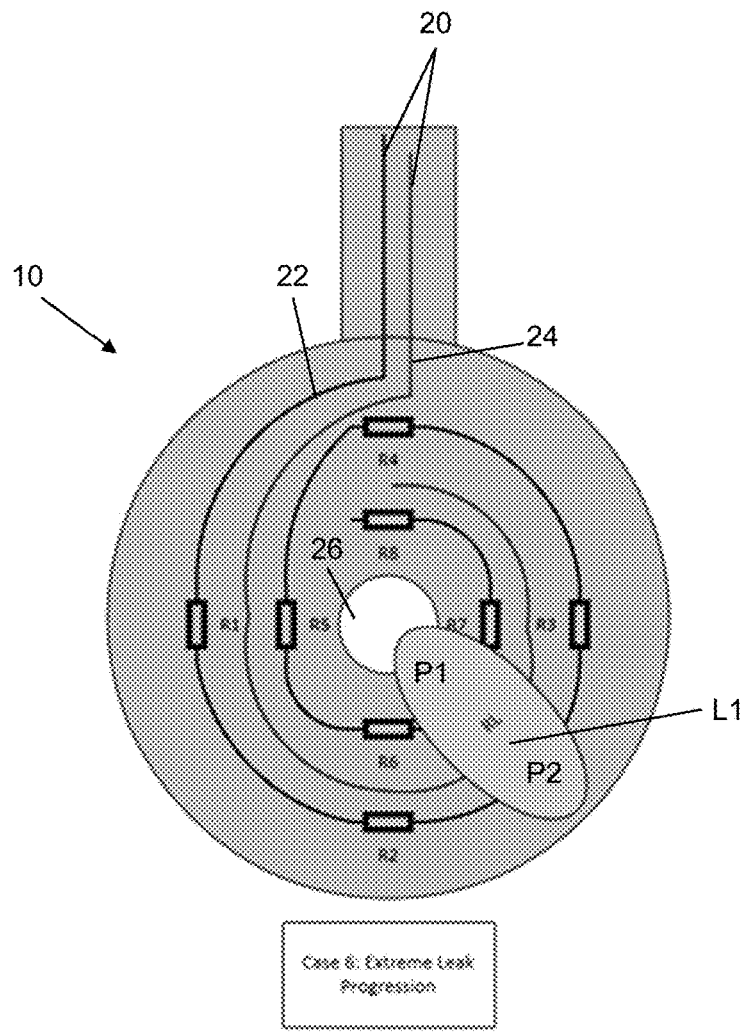
FIG. 5 is a diagram illustrating a plan view of a sensor device and an example of an ostomy effluent leak according to an embodiment.

FIG. 5 is a diagram illustrating a plan view of a sensor device 10 and an example of an ostomy effluent leak L1 according to an embodiment. The ostomy effluent leak L1 may be located at multiple positions P1, P2 and may have a generalized electrical resistance RL. The ostomy effluent leak L1 as shown in FIG. 5 may be considered to be an extreme leak.

Figure 6:
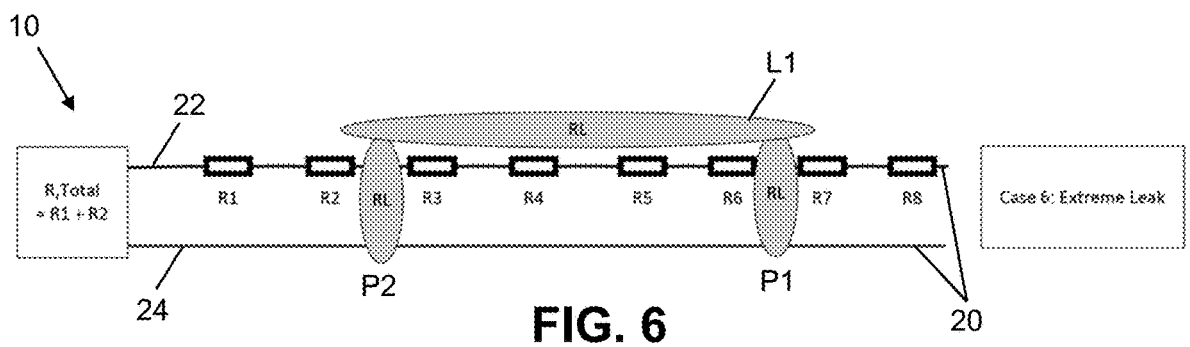
FIG. 6 is a schematic diagram illustrating the sensor device of FIG. 5 with the ostomy effluent leak disposed relative to electrically conductive circuitry of the sensor device.

FIG. 6 is a schematic diagram illustrating the sensor device 10 of FIG. 5 with the ostomy effluent leak L1 disposed relative to electrically conductive circuitry 20 of the sensor device 10. As shown in the examples of FIGS. 5 and 6, the ostomy effluent leak L1 may extend from the stoma opening 26 across the first electrode 22 between a sixth resistor R6 and a seventh resistor R7 at location P1 and between second resistor R2 and third resistor R3 at location P2. The ostomy effluent leak L1 may bridge the first and second electrodes 22, 24 between a first, or inner, wrap of the first electrode 22 and the wrap of the second electrode 24, and further bridge between the second electrode 24 and a second, or outer, wrap of the first electrode 22. In the example of FIG. 6, the total resistance $R_{TOTAL}$ may be approximated as:

$$R_{TOTAL} \approx R1 + R2$$

Figure 7:
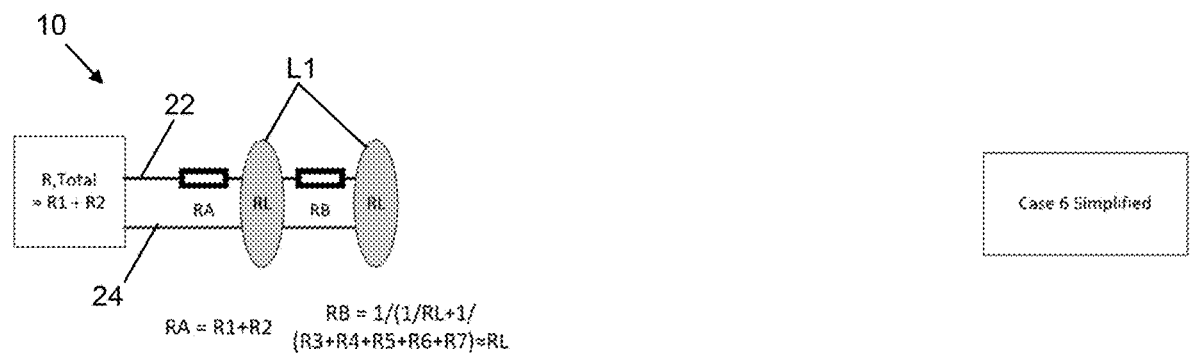
FIG. 7 is a simplified version of the schematic diagram of FIG. 6.

FIG. 7 is a simplified version of the schematic diagram of FIG. 6. In the example of FIG. 7, the total resistance $R_{TOTAL}$ may be approximated as:

$$R_{TOTAL} \approx R1 + R2$$

Further, in FIG. 7, RA and RB may be represented as:

$$RA = R1 + R2; \text{ and}$$

$$RB = 1/((1/RL) + (1/(R3 + R4 + R5 + R6 + R7))) \approx RL$$

In an embodiment, a single ostomy effluent leak L1 may present itself as two bridges, as shown in the example of FIG. 6. However, an extent of an ostomy effluent leak, and therefore the risk of leakage may be distinguished by the relatively low total resistance. Additionally, a device monitoring a progression of leakage may identify the pattern of progression, for instance, from the example shown in FIGS. 3 and 4 to the example shown in FIGS. 5-7 to further confirm the location of the leak.

In embodiments, an ostomy effluent leak bridging the first and second electrodes 22, 24 and having a generalized electrical resistance RL may form an electrical circuit having one or more resistors R1, R2 . . . Ri disposed in series or parallel with the generalized resistance RL of the ostomy effluent leak. The total resistance may be calculated, measured or estimated and compared to one or more stored resistance values corresponding to known ostomy effluent leak position, relative to the resistors R1, R2 . . . Ri of the first electrode 22. In an embodiment, the locations of the resistors R1, R2 . . . Ri on the sensor device 10, for example, relative to the stoma opening 26 may be known as well. Accordingly, the sensor device 10 may identify the location of an ostomy effluent leak.

Figure 8:
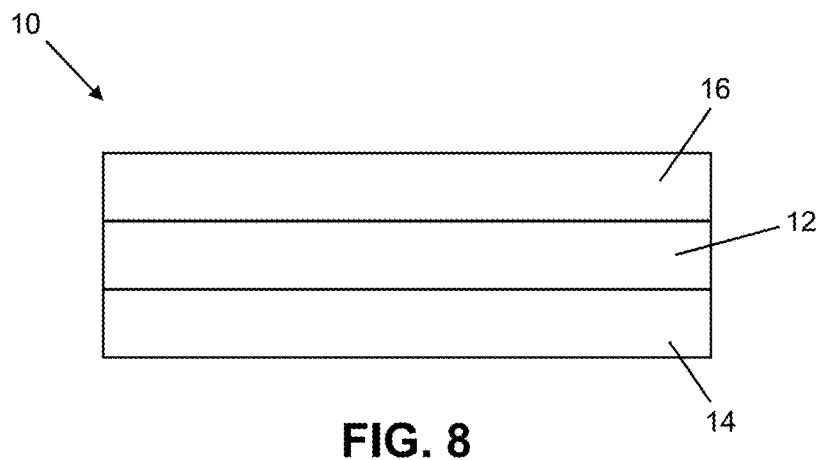
FIG. 8 is a schematic diagram illustrating an example of a sensor device according to an embodiment.

FIG. 8 is a schematic cross-sectional diagram illustrating an example of a sensor device 10 according to an embodiment. The electrically conductive circuitry 20 may be a sensor layer 12 of the sensor device 10. The sensor device 10 may further include a substrate layer 14 onto which the electrically conductive circuitry 20 may be applied. The substrate layer 14 may be, for example, a film, such as a polymeric film or an adhesive material. The electrically conductive circuitry 20 may be applied on the substrate layer 14 in any known, suitable manner. For example, the electrically conductive circuitry 20 may be printed on the substrate layer 14 using a suitable electrically conductive ink.

The sensor device 10 may also include an adhesive layer 16. The adhesive layer 16 may include, for example, a hydrocolloid material. In an embodiment, the sensor layer 12 may be disposed between the adhesive layer 16 and the substrate layer 14. The substrate layer 14 may be a distal side or pouch side of the sensor device 10 and the adhesive layer 16 may be a proximal side or body side of the sensor device 10.

In an embodiment, the sensor device 10 may integrated with an ostomy appliance (not shown), such as an ostomy barrier or faceplate configured to secure an ostomy pouch to a user. In an embodiment, the sensor device 10 may be provided as an ostomy accessory (not shown) which may be attached to an ostomy appliance. For example, the distal side of the sensor device may be secured to a body side of an ostomy barrier, and the proximal side of the sensor device may be adhered to the user.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular. In additions, various features described with respect to any of the embodiments above may be used together, implemented in, or replace features in any of the other embodiments described above.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. A sensor device for a medical appliance for detecting an effluent leakage comprising an electrically conductive circuitry, the electrical conductive circuitry comprising a first electrode and a second electrode spaced from the first electrode, wherein the first electrode is subdivided by a plurality of resistors spaced along a length of the first electrode, wherein the second electrode extends as a continuous strip of conductive material; and a controller operably connected to the sensor device, wherein the controller is configured to detect an electrical resistance in the electrically conductive circuitry, determine a change in the electrical resistance between the first and second electrodes as a function of time based on the detected electrical resistance, and determine whether an effluent leakage is present based on the detected electrical resistance.

2. The sensor device of claim 1, wherein the controller is further configured to identify a location of an effluent leakage based on the detected electrical resistance.

3. The sensor device of claim 1, wherein the plurality of resistors comprises R1, R2 and R3, and an effluent leakage has a generalized leak resistance RL, wherein a total resistance (Rtotal) of the electrically conductive circuitry drops when an effluent leakage bridges the first and second electrodes, wherein Rtotal when no effluent leakage bridges the first and second electrodes is at least 10 times greater than Rtotal when an effluent leakage bridges the first electrode and the second electrode.

4. The sensor device of claim 3, wherein Rtotal when an effluent leakage bridges the first and second electrodes between R1 and R2 is R1+RL.

5. The sensor device of claim 3, wherein Rtotal when an effluent leakage bridges the first and second electrodes between R2 and R3 is R1+R2+RL.

6. The sensor device of claim 3, wherein Rtotal when an effluent leakage bridges the first and second electrodes beyond R3 is R1+R2+R3+RL.

7. The sensor device of claim 1, wherein the sensor device is configured to detect an ostomy effluent leakage and includes an opening for receiving a stoma, wherein the first electrode and the second electrode are arranged in a spiral pattern around the opening, wherein the sensor device is configured to determine a progress of an ostomy effluent leakage, wherein the ostomy effluent leakage progresses from proximate the opening to an outer periphery of the sensor device.

8. The sensor device of claim 7, wherein the first electrode is arranged in a spiral pattern having a plurality wraps around the opening, and the second electrode extends between the wraps of the first electrode, wherein the first electrode is arranged to have more wraps than the second electrode, wherein a radially innermost wrap and a radially outermost wrap are both formed by the first electrode.

9. The sensor device of claim 8, wherein the plurality of resistors comprises R1, R2 . . . Rn−2, Rn−1 and Rn, wherein the Rn is arranged on the radially innermost wrap of the first electrode, wherein Rn−1 is arranged adjacent and spaced apart from Rn, Rn−2 is arranged adjacent and spaced apart from Rn−1, and R1 is arranged on the outermost wrap of the first electrode.

10. The sensor device of claim 9, wherein the sensor device is configured to detect a moderate leak when an ostomy effluent leakage bridges an innermost wrap of the first electrode and the second electrode.

11. The sensor device of claim 10, wherein Rtotal when an effluent leakage bridges the first and second electrodes between Rn−1 and Rn−2 is R1+R2 . . . +Rn−2+RL.

12. The sensor device of claim 9, wherein the sensor device is configured to detect a critical leak when an ostomy effluent leakage bridges an outermost wrap of the first electrode and the second electrode.

13. The sensor device of claim 12, wherein Rtotal when an effluent leakage bridges the first and second electrodes between R2 and R3 is approximately R1+R2.

14. The sensor device of claim 1, wherein the sensor device further comprises an adhesive layer configured to attach the sensor device to a user's skin.

15. The sensor device of claim 14, wherein the sensor device further comprises a substrate layer, wherein the electrically conductive circuitry is arranged between the substrate layer and the adhesive layer.

16. The sensor device of claim 1, wherein the sensor device is an ostomy accessory, wherein a distal side of the sensor device is secured to a body side of an ostomy barrier.

17. The sensor device of claim 14, wherein the adhesive layer is formed from a hydrocolloid adhesive.

18. The sensor device of claim 1, wherein the controller comprises a processor and a memory, wherein the processor is configured to execute program instructions and perform operations based on the executed program instructions.

19. The sensor device of claim 18, wherein the memory is configured to store resistor information, wherein the resistor information comprises a resistance and a position of each of the plurality of resistors.

20. The sensor device of claim 19, wherein the resistor information further comprises the detected electrical resistance including a series of detected electrical resistances detected as a function of time.

* * * * *